United States Patent [19]

Unruh et al.

[11] 4,193,943
[45] Mar. 18, 1980

[54] HYDROFORMYLATION CATALYSTS

[75] Inventors: Jerry D. Unruh; William J. Wells, III, both of Corpus Christi, Tex.

[73] Assignee: Celanese Corporation, New York, N.Y.

[21] Appl. No.: 898,734

[22] Filed: Apr. 24, 1978

Related U.S. Application Data

[63] Continuation of Ser. No. 650,405, Jan. 19, 1976, abandoned, which is a continuation-in-part of Ser. No. 569,738, Apr. 21, 1975, abandoned.

[51] Int. Cl.² .............................................. C07C 45/08
[52] U.S. Cl. ................................................ 260/604 HF
[58] Field of Search ................................... 260/604 HF

[56] References Cited

U.S. PATENT DOCUMENTS

| | | | |
|---|---|---|---|
| 3,239,566 | 3/1966 | Slaugh | 260/604 HF |
| 3,351,666 | 11/1967 | Mertzweiller et al. | 260/604 HF |
| 3,480,659 | 11/1969 | Dewhirst | 260/465.1 |
| 3,488,296 | 1/1970 | Senn et al. | 252/431 |
| 3,511,880 | 5/1970 | Booth | 260/604 HF |
| 3,939,188 | 2/1976 | McVicker | 260/429 |
| 3,965,192 | 6/1976 | Booth | 260/598 |
| 3,978,101 | 8/1976 | Aviron-Violet | 260/429 |
| 3,981,925 | 9/1976 | Schwager et al. | 260/604 HF |

FOREIGN PATENT DOCUMENTS 2359101 6/1974 Fed. Rep. of Germany ........... 260/604

OTHER PUBLICATIONS

Tetrahedron Letters, No. 14, pp. 1133–1134 (1976), Hayashi et al.
Tetrahedron Letters, No. 49–50, pp. 4405–4408 (1974), Hayashi et al.
Tetrahedron Letters, No. 21, pp. 1799–1802 (1977), Zembayashi et al.
Tetrahedron Letters, No. 48, pp. 4351–5354 (1976), Hayashi et al.
Tsuji et al., Bull. Soc. Chem., Japan, vol. 42, pp. 527–529 (1968).
Wilkinson, G. Bull. Soc. Chem. Trans., pp. 5055–5058 (1968).

Primary Examiner—Werren B. Lone
Attorney, Agent, or Firm—Kenneth A. Genoni; Ralph M. Pritchett

[57] ABSTRACT

An organo metallic complex catalyst, useful in the hydroformylation of an olefin, e.g., an alkene, to yield an aldehyde product in which the normal aldehyde isomer predominates over branch-chain isomers, which has the structure:

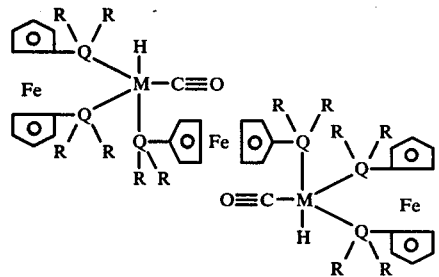

wherein capital M is a Group VIII metal (preferably rhodium); Q is phosphorus, arsenic, or antimony (preferably phosphorus); and R is phenyl or a lower alkyl group.

In the process employing the new catalytic complex is not necessary to employ an excess of any ligand, and moderate reaction conditions are adequate. The catalyst can be prepared ex situ or in situ from a suitable source of rhodium or the Group VIII metal and a suitable derivative of ferrocene.

50 Claims, No Drawings

HYDROFORMYLATION CATALYSTS

This is a continuation of application Ser. No. 650,405 filed Jan. 19, 1976 now abandoned which is a continuation-in-part of application Ser. No. 569,738 filed Apr. 21, 1975 now abandoned.

BACKGROUND OF THE INVENTION

It is disclosed in the above-identified patent application Ser. No. 569,738 that useful hydroformylation catalysts can be prepared by introducing into the hydroformylation reaction zone a mixture of (a) a disubstituted ferrocene and (b) a Group VIII compound as exemplified by the following:

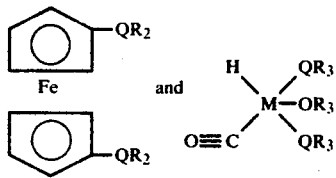

wherein M is a Group VIII metal, preferably rhodium; Q is phosphorus, arsenic, or antimony, preferably phosphorus; and R is phenyl or a lower alkyl group, preferably phenyl.

The catalytic complex resulting from the above-summarized combination (or from equivalent formulations also discussed in said application Ser. No. 569,738) is, broadly speaking, a complex cyclic structure containing one mole of the above-described substituted ferrocene and one mole of the abovedescribed Group VIII compound.

It has now been discovered, however, that, although the catalyst formed by reacting one mole of ferrocene derivative with one mole of Group VIII (e.g., rhodium) derivative as described above can be employed as a hydroformylation catalyst, the best results obtained in working with complexes of this general type are with formulations in which the molar ratio of ferrocene derivative to Group VIII metal is 1.5:1 rather than 1:1. This has led to the realization that the optimum catalyst in these ferrocene-derived complexes is a different one from those previously envisioned. It is a more complicated molecule, as will be further explained hereinbelow, although the procedures for forming it and for employing it in hydroformylation reactions are closely related to those used in preparing the 1:1 molar ratio complexes.

SUMMARY OF THE INVENTION

In accordance with the present invention an olefin, e.g., an alkene, is hydroformylated to produce an aldehyde product in which the normal aldehyde isomer predominates, without the necessity of employing an excess of any ligand species, by employing as hydroformylation catalyst a complex having the following structure, hereinafter designated "Complex A" for simplicity of presentation.

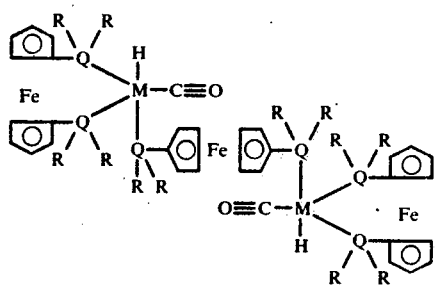

wherein M is a Group VIII metal, preferably rhodium; Q is phosphorus, arsenic, or antimony, preferably phosphorus; and R is phenyl or alkyl, preferably phenyl.

Alternatively, any of several rhodium sources are reacted with a suitable substituted ferrocene (e.g. and in particular triphenylphosphine-substituted ferrocenes), according to procedures which will be further explained hereinbelow, to produce the desired catalytic complex.

The catalytic complex can be prepared either in situ or ex situ.

It will thus be seen that the object of the present invention is to provide an improved catalyst for employment in hydroformylation reactions as well as providing improved processes for the hydroformylation of olefins. Other objects will be apparent from the following detailed description.

DETAILED DESCRIPTION OF THE INVENTION

The following will be divided into sections directed to (1) the improved catalytic complexes of the present invention, (2) processes for forming the improved complexes, and (3) hydroformylation processes employing the improved complexes.

THE IMPROVED CATALYTIC COMPLEXES

As summarized above, the improved catalytic Complex A described herein is preferably one in which M is rhodium, Q is phosphorus, and R is phenyl. Complexes which are suitable, although of lower activity, may be formed using other Group VIII metals, i.e., iron, cobalt, nickel, ruthenium, palladium, osmium, iridium, or platinum. The complex may, as indicated above, be formed in-situ in the hydroformylation reaction zone or, alternatively, it may be prepared ex-situ and subsequently introduced into the reaction zone with the appropriate hydroformylation reactants.

Complex A has been prepared and utilized, as will be described hereinbelow, but it has not actually been isolated in pure form. Its structure has been deduced from the following evidence:

Two complexes, previously discovered by the present applicants to have catalytic properties in hydroformylation reaction systems, have in fact been isolated and their structures determined. The first of these, to be referred to hereinbelow as "Complex (1)", has the following structure:

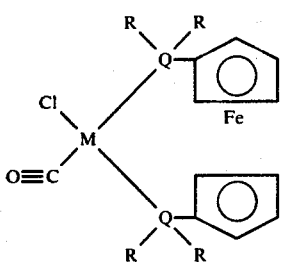

This Complex 1 is reacted, either in-situ or prior to introducing it into the hydroformylation reaction zone with a hydride source such as hydrogen and with a base such as sodium hydroxide to remove the chlorine atom, the resulting product (the hydrido derivative) then acting to catalyze the hydroformylation reaction.

Alternatively, it has also been previously discovered that there is another complex, which is also effective as a hydroformylation catalyst but which does not require pretreatment with a base before utilization as a catalyst, which has a structure as follows and which will be referred to hereinbelow as "Complex 2":

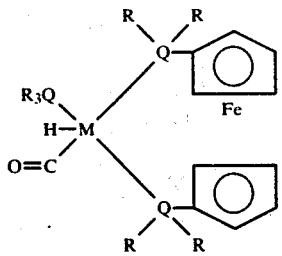

Both Complex 1 and Complex 2 have been identified and their catalytic utility demonstrated. In particular, for both of these type compounds, specific identification has been made for the species in which M is rhodium, Q is phosphorus, and R is phenyl.

Experimentation with these above-described complexes has demonstrated, however, that a very sharp change in their catalytic behavior takes place when (specifically in the case of the species in which M is rhodium, Q is phosphorus, and R is phenyl) there is incorporated into the reaction system an additional quantity of a diphenylphosphino-disubstituted ferrocene in an amount such that there is added to the complex an additional 0.5 mole of the ferrocene derivative per equivalent of rhodium contained in the original Complex 1 or Complex 2 as the case may be. In the case of Complex 1 this change was observed upon adding a hydroformylation reaction containing the hydrido form of the complex, to an additional 0.5 mole of bis(diphenylphosphino) ferrocene. In the case of Complex 2 identical results were obtained. In this same connection it might be noted that Complex 1 and Complex 2 are closely related, the reaction of Complex 1 with a mole of triphenylphosphine in the presence of a hydride source such as sodium borohydride resulting in the formation of Complex 2.

To continue with the phenomena which are observed when additional ferrocene is incorporated into the molecule of either Complex 1 or Complex 2, it has been discovered that, in the hydroformylation of an alkene, under typical hydroformylation reaction conditions in the presence of a mixture of hydrogen and carbon monoxide, the addition of the additional 0.5 mole of the substituted ferrocene causes a very sharp increase in the efficiency of conversion of the alkene of the corresponding aldehyde having one additional carbon atom. Specifically, in a typical 1-hexene hydroformylation run, the efficiency to heptanal was about 82% when the ratio of ferrocene moiety to rhodium atoms in the reaction zone was 1.5, whereas the efficiency was only 52% when the ratio was 1:1. At the intermediate ratio of ferrocene to rhodium of 1.25, the efficiency to heptanal was little changed, being about 53%. Likewise, increasing the ratio above 1.5 had practically no additional effect, the efficiency to heptanal being only about 0.5 percentage point higher when the ratio was 3.0:1 as compared with 1.5:1. There was also a corresponding dramatic improvement in the ratio of normal aldehyde to branched aldehydes in the reaction product, the ratio of normal to branched chain product being approximately 2.2:1 when the ferrocene:rhodium ratio was 1:1 while this normal:branch chain ratio was much higher (about 5.2:1) when the ferrocene: rhodium ratio was 1.5:1. As was the case with the efficiency to heptanal, the normal:branch chain aldehydes ratio also increased little or not at all (after the initial increase to 5.2:1) when the ferrocene:rhodium ratio was further increased above 1.5:1, i.e., when it was increased to 3.0:1. Isomerization of the 1-hexene raw material to the undesired 2-hexene was also drastically reduced at the 1.5:1 ferrocene:rhodium ratio as compared with 1.0:1. Quite aside from the fact that the above-described changes attendant upon the incorporation of the additional 0.5 mole of substituted ferrocene are highly desirable from the technical standpoint, the sharp and dramatic increase which results from adding this additional 0.5 mole of ferrocene moiety indicates clearly, when taken together with the fact that further increments of ferrocene moiety have no effect although they are not harmful, that there has been formed a new complex as opposed to, for example, some previously-unrealized benefit of simply increasing a ligand concentration in an equilibrium-type reaction (which latter effect would be more gradual and would not show the sudden "step" effect which characterizes the present system). In the light of these facts it is manifest that two moles of Complex 1 or Complex 2, as the case may be, have reacted with one mole of the substituted ferrocene to form a new complex, it being understood, of course, that a chloride scavenger such as sodium hydroxide is required in the case of Complex 1. It will also be seen that the mole of "bridging" substituted ferrocene would attach to Complex 1 or Complex 2 at the rhodium atom rather than at some other location inasmuch as the hydrido species resulting from removal of the chlorine atom from Complex 1 would be coordinatively unsaturated at the rhodium atom, making this the point at which further complexation, as by the substituted ferrocene, would occur. Likewise, in the case of Complex 2, it is manifest that the triphenylphosphine group initially attached to the rhodium atom would be displaced by the substituted ferrocene, since the electron-rich ferrocene moiety, attached to the phenylphosphino substituent, would make it more basic than the simple triphenylphosphine moiety originally present in Complex 2 and so result in displacement of the triphenylphosphine from the complex to form the bridged Complex A:

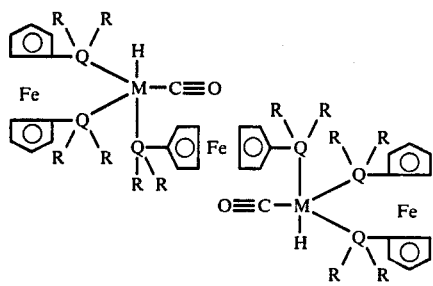

It is believed that the foregoing is a sound description of the nature of Complex A. Regardless of the correctness of these deductions, however, the present invention also embraces within its scope specific procedures for preparing the new catalytic complex, regardless of its exact structure, as will be explained hereinbelow.

Broadly speaking, and regardless of the exact structure of the present improved catalyst, it can be described as the hydrido carbonyl of a Group VIII metal, preferably rhodium, in complex combination with a ferrocene derivative of the structure

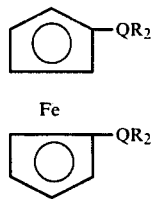

wherein Q is P, As, or Sb, preferably P, and R is phenyl or lower alkyl, preferably phenyl. It will be understood that the several "R" groups need not be identical. To form the preferred catalyst Complex A, it is necessary that 1.5 moles of the ferrocene derivative be complexed with each atom of rhodium. Proportions lower than 1.5:1 will form catalytic complexes within the scope of the invention, but the proportion of 1.5:1 leading to Complex A is preferred. Proportions higher than 1.5:1 are not disadvantageous, and are useful in actual hydroformylation reaction systems in order to ensure that there is enough of the ferrocene derivative present to satisfy the 1.5:1 requirement.

PROCESSES FOR FORMING THE IMPROVED CATALYSTS

In the following discussion rhodium, which is in any case the preferred member of the group, is to be understood as being representative of Group VIII metals in general. Likewise phosphorus, which again is the preferred member of the group of elements consisting of phosphorus, arsenic, and antimony, is to be understood as being representative of this group; that is, the phosphines are to be taken as being representative also of the arsines and the stibines. And, finally, the phenyl group is to be taken as being representative of the group consisting of phenyl and lower alkyl groups. Lower alkyl in the present context refers to alkyl groups having up to about 12 carbon atoms, although there is no real limitation on the size of alkyl groups which can be employed in formulating the present catalysts so long as they are available, or can be made available, as substituents in alkyl phosphines.

Broadly, the most preferred of the present catalysts are prepared by reacting one mole of a suitable rhodium source with carbon monoxide (if the rhodium source is not already a carbonyl) and with 1.5 moles of a 1,1'-bis(-dialkyl or diaryl phosphino) ferrocene, preferably and for example 1,1'-bis(diphenylphosphino) ferrocene, which in the following discussion will be used by way of example. The product of this broadly-described reaction is Complex A. Specific procedures will be summarized hereinbelow, but a few generalized comments are applicable to the over-all reaction regardless of individual steps which may be employed. More particularly:

The amount of processing required in converting the rhodium to the desired Complex A depends upon the nature of the initial rhodium source. For example, the rhodium in Complex A is in the $Rh^{+1}$ valence state, and if the rhodium in its original form is a common salt in which rhodium is the cation, it may be in the $Rh^{+3}$ valence state and must, therefore, at some stage in the complex-forming process be reduced. This reduction is normally accomplished by either carbon monoxide (which is present inherently in the hydroformylation reaction zone in which the catalyst is to be employed) or, alternatively, by phosphine ligands (e.g. triphenylphosphine). Rhodium sources which are initially in the $Rh^{+1}$ state do not need a specific reduction step. With further reference to this matter of reducing the rhodium, it has also been discovered that rhodium compounds having a halogen atom in the molecule, e.g., a chlorine atom, require the employment of a halide scavenger in connection with the reduction to eliminate from the system the halogen acid which is formed in the reduction and to form the rhodium-hydride complex. This is accomplished by either hydrogen (which is present inherently in the hydroformylation reaction zone in which the catalyst is to be employed) or, alternatively by an equivalent source of hydrogen such as a hydride (e.g., sodium borohydride). While a simultaneous reaction of a primary rhodium source with carbon monoxide and with the disubstituted ferrocene to form the desired Complex A can be envisioned, it is preferred to convert the rhodium source (e.g., a rhodium salt of a mineral acid or a carboxylic acid) to a carbonyl derivative as a first step, followed by subsequently reacting the carbonyl derivative with the disubstituted ferrocene to form Complex A. Obviously also, if the primary rhodium source is already the carbonyl or a carbonyl-containing compound such as a chlorocarbonyl, the initial carbonylation step is dispensed with.

Suitable rhodium sources which do not already comprise a carbonyl moiety in the molecule include the simple salts such as the halides (especially rhodium trichloride trihydrate), rhodium sulfate, rhodium nitrate, and rhodium carboxylates including the rhodium salts of simple carboxylic acids and dicarboxylic acids. Rhodium sources already containing carbonyl moiety in the molecule include $Rh_6(CO)_{16}$ and rhodium carbonyl chloride dimer. The material known in the trade as "rhodium on carbon", which comprises a mixture of rhodium oxides of a rather complex nature on a carbon support, can also be employed.

Some specific methods for preparing Complex A include the following:

(a) When the rhodium is initially available in a non-carbonyl form, the first step is to convert the rhodium to a carbonyl derivative by reaction with carbon monoxide. This can be done by any art-recognized method, the particulars of which are outside the scope of the present invention, but as typically exemplified by the procedures set forth in "Inorganic Synthesis", Vol. 8, p. 211 (1966). This carbonylation step can be carried out ex-situ, or it can be accomplished in-situ in the hydroformylation reaction zone. The rhodium carbonyl derivative so formed is then reacted with the disubstituted ferrocene derivative, one atom of rhodium moiety in the rhodium carbonyl derivative being reacted with one mole of the ferrocene derivative to form Complex 1 (the structure of which is set forth hereinabove), with the further addition of an additional 0.5 mole of the ferrocene derivative per mole of the Complex 1 then converting the Complex 1 to the desired Complex A. It will be understood that all of the ferrocene derivative can be added simultaneously, as distinguished from adding it in two increment whereby Complex 1 is formed as a first step to be then further converted to Complex A in a second step. As explained hereinabove, it is necessary to reduce $Rh^{+3}$, when it is present, to $Rh^{+1}$ to obtain the desired Complex A. This can be done during the course of reacting the primary rhodium source with the disubstituted ferrocene, or it can be done after the disubstituted ferrocene has been added by, for example, simply exposing the mixture of rhodium carbonyl derivative with the disubstituted ferrocene, within the hydroformylation reaction zone, to the hydrogen:carbon monoxide mixture which is employed in the course of the hydroformylation reaction. When a halide atom is present in the rhodium-containing moiety it is necessary to employ a halide scavenger, such as a base, to remove the halogen acid which is formed in the course of the hydrogenation. This halogen scavenging can be carried out simultaneously with the hydrogenation and the desired over-all result can be obtained by, for example, using an alkaline borohydride as a combination hydrogenation agent and halide scavenger.

(b) When the rhodium is initially available in the form of a carbonyl derivative, the carbonyl derivative can be reacted directly with the disubstituted ferrocene, in a proportion of 1.5 moles of the disubstituted ferrocene per atom of rhodium contained in the rhodium carbonyl derivative, to prepare Complex A directly in a single step. All these complexation reactions will be understood, of course, to take place in the liquid phase. When the rhodium carbonyl derivative is rhodium carbonyl chloride dimer, which is specifically useful for the purpose, the reaction between it and the disubstituted ferrocene is carried out in the presence of a chloride scavenger (as exemplified by sodium hydroxide, which is particularly useful) and a hydride source such as hydrogen or a borohydride. Rhodium carbonyl itself can be employed in the same manner, the chloride scavenger not being necessary in this case, (c) A third alternative is to react one mole of hydridocarbonyltris-(triphenylphosphine)rhodium(I) with 1.5 moles of 1,1'-bis(diphenylphosphino) ferrocene to produce Complex A directly without the necessity of employing either a reducing agent or a chloride scavenger.

(d) Finally, Complex (1) can be reacted with one mole of triphenylphosphine in the presence of a chloride scavenger and a suitable hydride source such as hydrogen, sodium borohydride (a combination hydride source and chloride scavenger), hydrazine (also a combination of hydride source and chloride scavenger), or any other common hydride source known to the art, to form Complex 2 as set forth hereinabove. The Complex 2 is then reacted with 0.5 mole of the 1,1'-bis(diphenylphosphino) ferrocene to produce Complex A.

The reactions entailed in the foregoing alternative procedures are all carried out in the liquid phase and in the presence of suitable inert solvents. It should also be mentioned that where triphenylphosphine (or its arsenic or antimony analogs) is referred to hereinabove, the organic moiety can be, instead of phenyl, a lower alkyl or cycloalkyl equivalent. Also, taking triphenylphosphine as exemplifying a preferred species, it is also possible to employ in place thereof other triorgano phosphorus compounds, e.g., triarylphosphites, trialkylphosphites, or tricycloalkylphosphites. Triphenylphosphine and triphenylphosphite are especially suitable, especially triphenylphosphine.

Concerning reaction parameters as they affect the above-summarized complexation reactions, it is to be understood that sufficient pressure must be maintained in order to maintain a liquid phase. If the complexes are to be formed in the hydroformylation reactor itself, within which the complex is to be employed as a catalyst, it will be understood that the hydroformylation reaction zone will itself always be maintained under sufficient pressure for this purpose. Likewise, the elevated temperatures always employed in hydroformylation reaction systems as already known to the art (e.g., temperatures in the range of about 25° C. to 150° C.) will always be in any event adequate to accomplish the complexation reactions, whichever of the above-described complexation reaction sequences is employed. As for the nature of the liquid phase in which the complexation reactions are to be carried out, the inert hydroformylation reaction solvents discussed hereinbelow under the heading "The Hydroformylation Reaction" are satisfactory. In some cases the intermediate complexes, or the rhodium sources from which they are derived, may not actually be in solution in the inert hydroformylation solvent, but in such cases the complexation reactions take place satisfactorily when such intermediates are simply kept in suspension by agitation. For example, "rhodium on carbon" is employed in the form of a suspension in the course of forming the desired complexes. Likewise, Complex 2 is not soluble in many of the hydroformylation solvents, but can be reacted with the disubstituted ferrocene to form Complex A in suspended solid form.

Some specific recommendations concerning reaction parameters to be employed in preparing Complex A and its intermediate precursors are summarized below, with it being understood that, in any case, the conditions of elevated temperature and pressure obtaining in the hydroformylation reaction zone are always adequate.

Concerning the procedures summarized in paragraph (a) above, the carbonylation of a non-carbonyl containing primary rhodium source to form the intermediate carbonyl derivative normally entails a reaction temperature of at least about 25° C. and a carbon monoxide partial pressure of at least about one atmosphere. A suitable inert solvent for the primary rhodium source is normally employed, e.g., ethanol, methanol, benzene, toluene, xylene, or diphenyl ether, although a reaction liquid can be employed in which the rhodium source is simply suspended rather than being dissolved. The subsequent conversion of the carbonyl intermediate to Complex 1, and the subsequent further conversion of Complex 1 to Complex A, is normally carried out at a temperature of about 25° C. or higher, up to the temperature range of about 100° C. to 150° C. at which the hydroformylation reaction itself is normally conducted. The rhodium reduction is normally conducted at a temperature of about 60° C. or higher. The halogen scavenging reactiong and resulting formation of the rhodium hydride complex is normally carried out at about 100° C. when base and hydrogen are used and at about 75° C. when sdium borohydride is used.

The reaction of the disubstituted ferrocene with the carbonyl intermediate, Complex 1, or Complex 2 takes place rapidly even at room temperature.

The reaction of Complex 1 with triphenylphosphine in the presence of a chloride scavenger and a hydride source to form Complex 2 as discussed above is advantageously carried out at a temperature of about 75° C. or higher.

The following examples are set forth to illustrate methods for forming the catalyst referred to herein as Complex A:

EXAMPLE 1

Following the procedure set forth in "Inorganic Synthesis", Vol. 8, p. 211 (1966), 1.35 millimoles of rhodium carbonyl chloride dimer was prepared and then mixed in 50 ml of benzene with 2.71 millimoles of 1,1'-bis(diphenylphosphino)ferrocene. When the evolution of gas from the reaction mixture had ceased, the remaining solution was reduced to dryness and the yellow solid which remained was placed in 200 ml of boiling ethanol. When the volume had been reduced to 170 ml by evaporation during the boiling process, the hot solution was filtered and the liquid was discarded. The beige-yellow solid remaining from the filtration was vacuum dried to produce a 90.0% yield of a solid product having a melting point of 183°-9° C. This final product was the Complex 1 described elsewhere hereinabove, in which M is rhodium, Q is phosphorus, and R is phenyl.

The Complex 1 obtained by the foregoing procedure is readily converted to Complex 2 (also described hereinabove) by being treated with sodium borohydride in the presence of a compound having the structure $QR_3$, wherein Q is phosphorus, arsenic, or antimony and wherein R is phenyl or lower alkyl. The following example illustrates this conversion of Complex 1 to Complex 2:

EXAMPLE 2

Complex 1 as obtained hereinabove (0.50 gram) is mixed in a flask with 0.20 gram of triphenylphosphine (a molar ratio of 1:1) in 20 ml of refluxing ethanol. There is then slowly added to the refluxing mixture 0.20 gram of sodium borohydride in 20 ml of ethanol to form a suspension of a red-brown solid. The solid is filtered out hot and then vacuum dried to yield, in 85.5% efficiency, a product having a melting point of 124°-9° C. This product is Complex 2.

EXAMPLE 3

Complex A is conveniently formed from Complex 1, produced as explained hereinabove, by a method which simply entails incorporating a quantity of the Complex 1 into a suitable art-recognized hydroformylation reaction solvent (e.g., toluene) along with 1,1'-bis(diphenylphosphino)ferrocene in an amount of 0.5 mole of the phosphino ferrocene for each mole of the Complex 1. A suitable chloride scavenger, e.g., and preferably, sodium hydroxide in aqueous solution, is also stirred into the mixture in an amount of at least one mole of the sodium hydroxide per mole of the Complex 1. When the resulting mixture is then further admixed with the reactants employed in a hydroformylation process (i.e., an alkene together with a mixture of hydrogen and carbon monoxide in a hydrogen: CO ratio of about 1:1) under hydroformylation reaction conditions (e.g., a temperature of about 80° C. and a superatmospheric pressure sufficient to maintain a liquid phase), the Complex 1 is converted in-situ to Complex A. It will be understood in this connection that sodium chloride is formed as a by-product which has no particular deleterious effect although it can be removed from the system if desired, and also that the hydrogen and carbon monoxide function, in addition to being hydroformylation reactants, as chemical agents in completing the conversion of the Complex 1 to Complex A.

It is also to be understood that the Complex 1, when reacted with the sodium hydroxide and the synthesis gas as described above but without the additional quantity of diphenylphosphino ferrocene as described above, is itself an active hydroformylation catalyst. However, reacting it with the additional 0.5 mole of diphosphino ferrocene as described herein converts it to the much more useful Complex A. The conversion of Complex 1 to Complex A can be carried out at any time during the course of operating a hydroformylation process in which the catalyst initially introduced into the reaction zone has been Complex 1. That is, a reaction system in which Complex 1 is the catalyst can be converted to one in which Complex A is the catalyst by simply, at any time, adding an additional 0.5 mole of the 1,1'-bis(-diphenylphosphino) ferrocene per mole of the Complex 1 which was initially introduced into the system. Likewise Complex 2, also described hereinabove, can be converted at any time in a hydroformylation reaction system to Complex A by simply adding the additional 0.5 mole of bis(diphenylphosphino) ferrocene/mole of rhodium in the same way. In this latter case, one mole of triphenylphosphine is released, in the resulting condensation reaction, per mole of Complex 2 which was initially present. This resulting free triphenylphosphine can remain in the system without adverse effect although it plays no part in the hydroformylation reaction.

THE HYDROFORMYLATION REACTION

In general, the hydroformylation of an olefin, e.g., an alkene, by the present process is effected by introducing into an ordinary reaction vessel or zone the olefin to be hydroformylated, a gaseous mixture of hydrogen and carbon monoxide, and either Complex A itself or else its precursors as explained hereinabove. That is, by "precursors" is meant either Complex 1 or Complex 2 or else the more fundamental reactans from which they themselves are formed, e.g., a rhodium source as described hereinabove and a disubstituted ferrocene such as the 1,1'-bis(diphenylphosphino) ferrocene along with a scavenger such as sodium hydroxide in those cases in which the rhodium is introduced as a chloride or other salt. There is also employed a reaction solvent in accordance with the well-known technology of hydroformylation chemistry, toluene being an example of a typical inert solvent used in these systems. Many other solvents can be employed, such as benzene, xylene, diphenyl ether, alkanes, aldehydes, and esters. Selection of the solvent is outside the scope of the present invention, which is drawn more particularly to improved catalysts for this reaction system rather than to other modifications of the system itself. In the reaction system the catalytic complex serves to catalyze the hydroformylation of the olefin with the hydrogen and the carbon monoxide to form a mixture of aldehydes containing one more carbon atom than the olefin reactant. Typically, it is desired to employ a terminally-unsaturated olefin, and it is normally preferred that the terminal carbon atom be the site of attachment of the carbonyl group which is introduced by the hydroformylation reaction. The nature of the catalyst employed affects this matter of whether a normal aldehyde is produced (i.e., whether the terminal carbon atom is the site of hydrocarbonylation as compared with the second carbon atom in the chain), and the present improved catalyst gives very good results in this regard. That is, it produces a high proportion of aldehyde product in which the terminal carbon atom has been hydroformylated.

A wide variety of olefins, especially olefins having up to about 25 carbon atoms, can be hydroformylated in accordance with the process of this invention to form aldehyde derivatives of said olefins having at least one additional carbon atom as compared with the parent olefin (di- or triethylenically unsaturated olefins being capable, of course, upon complete hydroformylation of forming derivatives having up to one additional carbon atom for each ethylenic double bond in the parent compound). Olefinic compounds having substituent groups, e.g., ethylenically unsaturated alcohols, aldehydes, ketones, esters, carboxylic acids, acetals, ketals, nitriles, amines, etc. can also be hydroformylated. Broadly, olefinic compounds which are free of substituent atoms other than oxygen and nitrogen are readily hydroformylated, especially such compounds having no substituent atoms other than oxygen. Some specific classes of substituted olefins to which the hydroformylation process is applicable are: unsaturated aldehydes such as crotonaldehyde; alkenoic acids such as acrylic acid; and unsaturated acetals, such as acrolein acetal. More commonly employed feedstocks include simple alkenes such as ethylene, propylene, and butylenes, etc.; alkadienes such as butadiene and 1,5-hexadiene, and their aryl, alkaryl, and aralkyl derivatives. Hydroformylation does not normally take place within the benzene ring of olefins having aryl substitution of course but rather in the ethylenically-unsaturated portion of the molecule.

Process operating parameters employed in the present invention will vary depending upon the nature of the end product desired. In general, however, the operating parameters contemplated by the present process are the same as those conventionally employed in prior art hydroformylation processes. For the sake of convenience, these parameters will be generally described hereinafter; it being understood, however, that the parameters are not critical to achieving the improved results of the present invention and do not per se form a part of the present invention.

In general, the hydroformylation process is conducted under a total reaction pressure of hydrogen and carbon monoxide of one atmosphere or less up to a pressure of about 1000 psig or more. For commercial reasons, however, pressures significantly greater than about 400 psig will not normally be employed.

The reaction is also normally conducted at a temperature of from about 50° to about 200° C. with a temperature within the range of from about 75° to about 150° C. being most usually employed.

The ratio of partial pressures of the hydrogen to carbon monoxide present in the reaction vessel may be from about 10:1 to 1:10, but will normally be from about 3:1 to about 1:3, with a hydrogen to carbon monoxide ratio of at least about 1:1 being preferred.

If desired, the reaction mixture may also contain other materials, such as an organic solvent as discussed hereinabove to act as a reaction medium for the olefin and the oil-soluble catalytic complex. Additional organic solvents are not required, however, since the olefin reactant also serves as a solvent.

The following examples are exemplary of hydroformylation reactions using the catalysts described hereinabove.

EXAMPLE 4

Table I below presents the results obtained in several laboratory runs in which the hydroformylation of 1-hexane was carried out in the presence of toluene as reaction solvent and in which the catalyst was Complex 1 initially, with additional quantities of 1,1'-bis(diphenylphosphino) ferrocene being added as indicated in amounts sufficient to convert Complex 1 to Complex A. Runs are included, as will be seen, in which more than enough of the diphenylphosphino ferrocene was added to form Complex A. In all cases enough sodium hydroxide was included in the reactor charge to scavenge the chloride moiety initially present in the Complex 1. In all cases the reactor charge comprised 60 ml of toluene, 20 ml of 1-hexene, and, initially, 0.2 millimole of the Complex 1. As already explained, additional amounts of the diphenylphosphino ferrocene were incorporated into some of the runs as shown in the Table. Each run was carried out by charging the toluene, the initial charge of catalyst in the form of Complex 1, additional ligand as indicated and the sodium hydroxide into a pressure autoclave, which was then closed and flushed several times with a 1:1 mixture of hydrogen and carbon monoxide. The autoclave was then pressured to about 1.3 atmospheres gauge and then heated to the indicated reaction temperature. The 1-hexene feedstock was initially contained in a pressurized feed reservoir and there heated to the same indicated reaction temperature prior to being introduced into the reaction autoclave. When both the autoclave and the hexene feed reservoir were at the desired reaction temperature, the 1-hexene was then quickly pressured into the autoclave, employing some of the 1:1 synthesis gas from a high-pressure synthesis gas reservoir as the pressurizing agent. The autoclave was then pressured to the desired reaction pressure with the 1:1 hydrogen:carbon monoxide synthesis gas from the synthesis gas reservoir. Upon attainment of the desired reaction pressure, the run was taken as having been started. That is, the time at which the reactor was brought to the desired pressure at the desired temperature was taken as "time zero". The progress of the reaction was then followed by the rate of pressure drop in the synthesis gas reservoir (which was always at a pressure higher than the autoclave pressure, whereby the autoclave could be maintaned at the desired pressure level.

When the rate of reaction had dropped to an extremely low level as indicated by a very low rate of decline of the pressure in the synthesis gas feed reservoir, the autoclave was cooled and its contents were removed and analyzed by chromatographic methods. The results, as shown in Table I below, show clearly that a sharp increase in catalyst efficiency took place when the ratio of total diphenylphosphino ferrocene moiety (including that initially present in the Complex 1) to rhodium atoms was 1.5:1 and that further increases were superfluous.

In Table I the identifying run numbers are those used in original records. The rhodium concentration is the concentration of rhodium introduced into the reaction system as Complex 1. The concentration of 1,1'-bis(diphenylphosphino) ferrocene, abbreviated in the Table as $Fc(P\Phi_2)_2$, is the total concentration of this moiety including both that initially introduced as part of the molecule of Complex 1 and also that which was introduced as an additional quantity of the diphenylphosphino ferrocene itself. The n/iso-aldehyde ratio is the ratio of heptanal to branched-chain isomers in the reaction product. Chemical efficiencies shown refer to the percentage of the 1-hexene consumed which was identified in the reaction product in the form of each of the named end products.

the Complex 2, whereby the ratio of diphenylphosphino ferrocene moiety to rhodium was 1.0:1. In the second run sufficient additional 1,1'-bis(diphenylphosphino) ferrocene was incorporated into the reaction medium to bring the ratio of diphenylphosphino moiety to rhodium atoms up to 2.0:1. In this example there was no need to employ a chloride scavenger (e.g., sodium hydroxide) and none was in fact employed. It will be seen that in the second of the runs shown, in which there was more than sufficient diphenylphosphino ferrocene moiety to convert Complex 2 to Complex A, dramatic improvement in results was obtained.

TABLE III

| Run No. | 20708-9 | 22959-39 |
|---|---|---|
| Rh conc., mM | 1.67 | 2.5 |
| $Fc(P\Phi_2)_2$ conc., mM | 1.67 | 5.0 |
| $Fc(P\Phi_2)_2$/Rh ratio | 1.0 | 2.0 |

TABLE I

| Run No. | 22959-14 | 22959-15 | 22959-19 | 22959-18 | 22959-34 | 22959-12 | 22959-16 | 22959-17 |
|---|---|---|---|---|---|---|---|---|
| Rh conc., mM | 2.5 | 2.5 | 2.5 | 2.5 | 2.5 | 2.5 | 2.5 | 2.5 |
| $Fc(P\Phi_2)_2$ conc., mM | 2.5 | 2.5 | 3.12 | 3.75 | 3.75 | 5.0 | 5.0 | 7.5 |
| $Fc(P\Phi_2)_2$/Rh ratio | 1.0 | 1.0 | 1.25 | 1.50 | 1.50 | 2.0 | 2.0 | 3.0 |
| Temp., °C. | 110 | 110 | 110 | 110 | 110 | 110 | 110 | 110 |
| Pres., psig (1:1 $H_2$:CO) | 150 ± 1 | 150 ± 1 | 150 ± 1 | 150 ± 1 | 150 ± 1 | 150 ± 1 | 150 ± 1 | 150 ± 1 |
| n/iso-aldehyde ratio | 2.22 | 2.12 | 2.76 | 5.12 | 5.21 | 5.16 | 5.25 | 5.19 |
| Conv., % | 99.9 | 99.9 | 98.6 | 98.6 | 96.8 | 95.3 | 98.8 | 99.1 |
| Eff. to prod., %: | | | | | | | | |
| Heptanal | 53.8 | 54.2 | 57.5 | 82.5 | 82.9 | 82.6 | 83.0 | 82.6 |
| 2-Methylhexanal | 24.2 | 25.6 | 20.8 | 16.1 | 15.9 | 16.0 | 15.8 | 15.9 |
| 2-Hexene | 21.0 | 19.2 | 20.8 | 0.5 | 0.5 | 0.6 | 0.5 | 0.6 |
| Hexene | 1.0 | 1.0 | 0.9 | 0.9 | 0.7 | 0.8 | 0.7 | 0.9 |

EXAMPLE 5

Another series of runs was carried out according to the same procedure set forth above in Example 4, except that reaction pressure was varied to explore the effect of this parameter. It will be seen that the ratio of diphenylphosphino ferrocene moiety to rhodium is slightly more than that required for the complete conversion of the Complex 1 to Complex A. This excess was employed to insure that conversion of Complex 1 to Complex A would in fact be complete in all cases whereby any uncertainty regarding nature of the catalyst complex could not obscure the experimental results.

The results, set forth in Table II below, indicate that optimum results were obtained at a reaction pressure of about 50 lb per square inch gauge.

TABLE II

| Run No. | 22959-47 | 22959-50 | 22959-46 | 22959-43 | 22959-12 | 22959-16 | 22959-41 | 22959-42 |
|---|---|---|---|---|---|---|---|---|
| Rh conc., mM | 2.5 | 2.5 | 2.5 | 2.5 | 2.5 | 2.5 | 2.5 | 2.5 |
| $Fc(P\Phi_2)_2$ conc., mM | 5.0 | 5.0 | 5.0 | 5.0 | 5.0 | 5.0 | 5.0 | 5.0 |
| $Fc(P\Phi_2)_2$/Rh ratio | 2.0 | 2.0 | 2.0 | 2.0 | 2.0 | 2.0 | 2.0 | 2.0 |
| Temp., °C. | 110 | 110 | 110 | 110 | 110 | 110 | 110 | 110 |
| Pres., psig (1:1 $H_2$:CO) | 32 ±2 | 40 ± 1 | 50 ± 1 | 101 ± 1 | 150 ± 1 | 150 ± 1 | 202± 2 | 300 ± 2 |
| n/iso-aldehyde ratio | 5.03 | 5.47 | 6.19 | 5.59 | 5.15 | 5.25 | 4.79 | 4.70 |
| Conv., % | 99.8 | 99.6 | 99.8 | 99.8 | 95.3 | 98.8 | 96.1 | 96.2 |
| Eff. to prod., %: | | | | | | | | |
| Heptanal | 65.3 | 80.9 | 84.3 | 83.8 | 82.6 | 83.0 | 81.5 | 81.7 |
| 2-Methylhexanal | 13.0 | 14.8 | 13.7 | 15.0 | 16.0 | 15.8 | 17.0 | 17.4 |
| 2-Hexene | 20.3 | 2.6 | 0.7 | 0.6 | 0.6 | 0.5 | 0.5 | 0.5 |
| Hexene | 1.4 | 1.7 | 1.3 | 0.6 | 0.8 | 0.7 | 1.0 | 0.4 |

| | | |
|---|---|---|
| Temp., °C. | 110 | 110 |
| Pres., psig (1:1 $H_2$:CO) | 100 ± 2 | 150 ± 1 |
| n/iso-aldehyde ratio | 2.46 | 5.01 |
| Conv., % | 94.9 | 99.7 |
| Eff. to prod., %: | | |
| Heptanal | 51.9 | 82.1 |
| 2-Methylhexanal | 21.1 | 16.4 |
| 2-Hexene | 27.0 | 0.4 |
| Hexene | tr | 1.1 |

EXAMPLE 7

Two runs were carried out employing the same procedure as set forth in Example 6 above, except that the rhodium source was the hydridocarbonyltris (triphenylphosphine) rhodium (I). As in Example 6, there is one run in which the diphenylphosphino ferrocene:rhodium

EXAMPLE 6

Two runs were carried out employing the same reaction procedure as set forth in the two preceding examples except that the rhodium source was Complex 2. In the first run shown below the only catalyst present was the Complex 2, whereby the ratio of diphenylphosphino ratio is 1.0, and a second run in which sufficient additional 1,1-bis(diphenylphosphino) ferrocene had been added to convert the hydridocarbonyltris(triphenylphosphine) rhodium (I) catalyst into Complex A. The results tabulated below indicate that the results obtained were substantially the same as those obtained in Example 6 in which the rhodium source was Complex 2. As in the case of Example 6 also, a dramatic improvement in results was obtained when sufficient diphenylphosphino ferrocene was incorporated into the catalyst system to convert the catalyst to Complex A.

TABLE IV

| Run No. | 22959-9 | 22959-40 |
|---|---|---|
| Rh conc., mM | 2.5 | 2.5 |
| Fc(PΦ$_2$)$_2$ conc., mM | 2.5 | 5.0 |
| Fc(PΦ$_2$)$_2$/Rh ratio | 1.0 | 2.0 |
| Temp., °C. | 110 | 110 |
| Pres., psig (1:1 H$_2$:CO) | 100 ± 2 | 150 ± 1 |
| n-iso-aldehyde ratio | 1.84 | 5.05 |
| Conv., % | 99.9 | 98.7 |
| Eff. to prod., %: | | |
| Heptanal | 54.2 | 82.3 |
| 2-Methylhexanal | 19.1 | 16.3 |
| 2-Hexene | 25.8 | 0.5 |
| Hexene | 0.9 | 0.9 |

EXAMPLE 8

The following illustrates a recommended procedure for preparing Complex A in which the initial rhodium source is a simple salt (rhodium trinitrate in this case) and in which the tendency of the simple salt to precipitate metallic rhodium when it comes into contact with the reducing atmosphere obtaining within the hydroformylation reaction zone is counteracted by employing a polyalkylene glycol coupling solvent as disclosed in U.S. Pat. Ser. No. 526,298 filed Nov. 22, 1974 by A. L. Stautzenberger et al. Use of the coupling solvent is generally recommended when the initial rhodium source is a simple rhodium salt.

Into an agitated autoclave there was placed, as the initial charge, 0.2 millimole of rhodium trinitrate, in the form of an aqueous solution containing 12.9% rhodium by weight admixed with 4.11 grams of diethylene glycol as coupling solvent, together with 60 ml of toluene and 0.2618 gram of triphenylphosphine (1.0 millimole). The autoclave was flushed several times with synthesis gas consisting of hydrogen and carbon monoxide in a 1:1 mole ratio, after which the autoclave was heated to 110° C. and stirred overnight at this temperature and under a synthesis gas pressure of 125 lb per sq. inch gauge. This converted the rhodium to a hydrido carbonyl complex with triphenylphosphine, the complex being of the formula

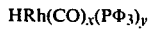

HRh(CO)$_x$(PΦ$_3$)$_y$ wherein x+y=4.

After the foregoing initial complexation reaction to form the hydrido carbonyl triphenylphosphine complex, the autoclave was cooled to room temperature and depressured. There was then added to the autoclave contents 0.35 millimole of 1,1'-bis(diphenylphosphino) ferrocene dissolved in 5 ml of toluene. Next, after resealing and bringing the autoclave to 110° C. again, 20 ml of 1-hexane was introduced into it. The autoclave was then brought to a pressure of 110 lb per sq. inch gauge with the same 1:1 synthesis gas mixture described more particularly hereinabove, and while being agitated was maintained at 110 lb per sq. inch gauge pressure for 335 minutes.

At the conclusion of the 335 minute reaction period the autoclave was cooled and depressured and its contents analyzed chemically. Of the 1-hexene initially charged, 93.8% was found to have been converted. The efficiency of conversion to heptanal was 80.0%, and the ratio of heptanal to the branched isomer was 5.07.

It should be noted that, in charging the autoclave, the triphenylphosphine was added before the disbustituted ferrocene to insure that it, rather than the ferrocene, would be oxidized by the trivalent rhodium. It is well known that rhodium (III) can be reduced to Rh(I) by employing triphenylphosphine as the reducing agent. It will also be noted that, with the nitrate salt of rhodium, an alkaline-reacting scavenger was not necessary.

EXAMPLE 9

A stirred autoclave was charged with 55 milliliters of toluene, 0.2 millimole of rhodium trichloride trihydrate, and 1.2 ml of 0.5 N sodium hydroxide. The mixture was then stirred at a temperature of 110° C. for one hour and under 150 lb per sq. inch gauge pressure of 1:1 hydrogen:carbon monoxide synthesis gas. There was then added to the autoclave 0.35 millimole of 1,1'-bis(diphenylphosphino) ferrocene dissolved in 5 milliliters of toluene.

To the autoclave there was next added 20 ml of 1-hexene, after which the autoclave was maintained for 140 minutes at a temperature of 110° C. under a synthesis gas pressure (1:1 hydrogen:carbon monoxide) of 100 lb per sq. inch gauge.

The autoclave was then cooled to ambient temperature, depressured, and its contents analyzed chemically. The conversion of the 1-hexene was determined to be 99.4%. The efficiency to normal heptaldehyde was 79.1%, and the efficiency to 2-methylhexanal was 15.5%.

EXAMPLE 10

Employing a stirred autoclave as in the preceding examples, the autoclave was charged with 60 ml of toluene, 0.35 millimole of 1,1'-bis(diphenylphosphino) ferrocene, and 0.5538 gram of "rhodium on carbon" which contained 3.72 weight percent rhodium on powdered activated carbon.

The autoclave was then sealed and flushed several times with 1:1 hydrogen:carbon monoxide synthesis gas after which the autoclave was brought to a pressure of 75 lb per sq. inch gauge and heated to 110° C., and the autoclave pressure was then brought to 100 lb per sq. inch gauge.

While being continuously stirred, the contents of the autoclave were then allowed to react for 60 minutes at a temperature of 110° C. and a pressure of 100 lb per sq. inch gauge.

The autoclave was then cooled to room temperature, depressured, and the contents analyzed. The conversion of the 1-hexene was determined to be 93.9%. The efficiency to heptanal was 78.6%, and the efficiency to 2-methylhexanal was 15.4%.

The embodiments of the invention in which an exclusive property or privilege is claimed are defined as follows:

1. In the hydroformylation of an olefin having up to about 25 carbon atoms with hydrogen and carbon monoxide in a liquid-phase reaction zone to produce an aldehyde derivative of said olefin, said hydroformylation being conducted at a temperature from about 50° C. to about 200° C., under a combined partial pressure of hydrogen and carbon monoxide of from about one atmosphere to about 1000 pounds per square inch, and with the ratio of hydrogen partial pressure to that of carbon monoxide being from about 10:1 to 1:10, the improvement which comprises catalyzing said hydroformylation with rhodium hydrido carbonyl in complex combination with a ferrocene derivative of the structure

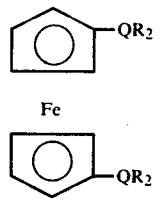

wherein Q is P, As, or Sb and R is phenyl or lower alkyl.

2. The improvement of claim 1 wherein Q is phosphorus.

3. The improvement of claim 2 wherein R is phenyl.

4. The improvement of claim 1 wherein there are maintained in said reaction zone at least about 1.5 moles of said ferrocene derivative per atom of rhodium and wherein said olefin is a member of the group consisting of alkenes, alkadienes, and aryl, alkaryl, and aralkyl derivatives thereof.

5. The improvement of claim 4 wherein said olefin is an alkene.

6. The improvement of claim 4 wherein there are maintained in said reaction zone from about 1.5 to about 3.0 moles of said ferrocene derivative per atom of rhodium.

7. The improvement of claim 4 wherein there are maintained in said reaction zone about 1.5 moles of said ferrocene derivative per atom of rhodium.

8. The improvement of claim 1 wherein the structure of the rhodium hydrido carbonyl in complex combination with the ferrocene derivative is

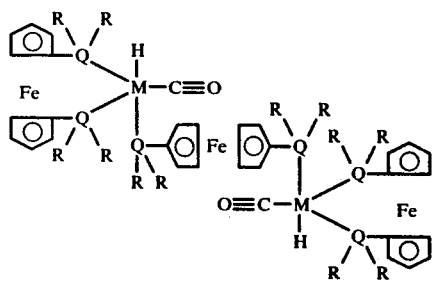

wherein M is rhodium and Q is phosphorus.

9. The improvement of claim 8 wherein R is phenyl.

10. The improvement of claim 1 wherein there are charged to the reaction zone:
a ferrocene derivative of the formula

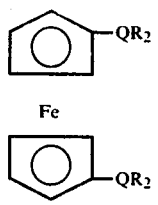

and a complex of the formula

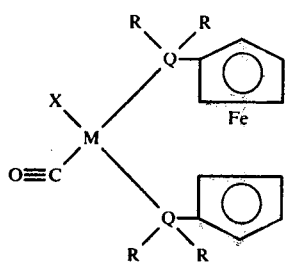

wherein M is rhodium and X is a halide, and a halide scavenger in an amount at least equivalent to the halide content of said complex, together with a hydride source.

11. The improvement of claim 10 wherein the hydride source is hydrogen and the halide is chloride.

12. The improvement of claim 11 wherein Q is phosphorus.

13. The improvement of claim 12 wherein R is phenyl.

14. The improvement of claim 10 wherein there is charged to the reaction zone at least about one-half mole of said ferrocene derivative per mole of said complex.

15. The improvement of claim 14 wherein there is charged to the reaction zone about one-half mole of said ferrocene derivative per mole of said complex.

16. The improvement of claim 1 wherein there are charged to the reaction zone:
a ferrocene derivative of the formula

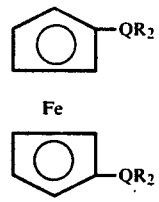

and a complex of the formula

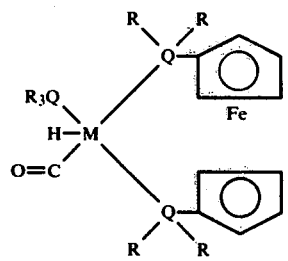

wherein M is rhodium.

17. The improvement of claim 16 wherein Q is phosphorus.

18. The improvement of claim 17 wherein R is phenyl.

19. The improvement of claim 16 wherein there is charged to the reaction zone at least about one-half mole of said ferrocene derivative per mole of said complex.

20. The improvement of claim 19 wherein there is charged to the reaction zone about one-half mole of said ferrocene derivative per mole of said complex.

21. The improvement of claim 1 wherein there are charged to the reaction zone a ferrocene derivative of the formula

Fe

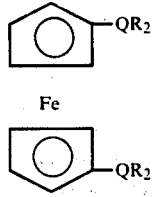

wherein Q is phosphorus and R is phenyl or lower alkyl
and a rhodium hydrido carbonyl complex of the formula

Rh(H)(CO)(X)$_3$ wherein X is triarylphosphine, trialkylphosphine, tricycloalkylphosphine, triarylphosphite, trialkylphosphite, or tricycloalkylphosphite.

22. The improvement of claim 21 wherein R is phenyl.

23. The improvement of claim 22 wherein X is triphenylphosphine.

24. The improvement of claim 21 wherein there are maintained in the reaction zone at least about 1.5 moles of said ferrocene derivative per atom of rhodium.

25. The improvement of claim 24 wherein there are maintained in the reaction zone about 1.5 moles of said ferrocene derivative per atom of rhodium.

26. In the hydroformylation of an olefin having up to about 25 carbon atoms with hydrogen and carbon monoxide in a liquid-phase reaction zone to produce an aldehyde derivative of said olefin, said hydroformylation being conducted at a temperature from about 50° C. to about 200° C. and under a combined partial pressure of hydrogen and carbon monoxide of from about one atmosphere to about 1000 pounds per square inch, and said olefin being selected from the group consisting of alkenes, alkadienes, and aryl, alkaryl, and aralkyl derivatives thereof, the improvement which comprises catalyzing said hydroformylation with rhodium hydrido carbonyl in complex combination with a ferrocene derivative of the structure

Fe

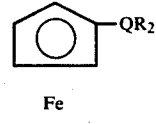

wherein Q is P, As, or Sb and R is phenyl or lower alkyl.

27. The improvement of claim 26 wherein Q is phosphorous.

28. The improvement of claim 27 wherein R is phenyl.

29. The improvement of claim 26 wherein there are maintained in said reaction zone at least about 1.5 moles of said ferrocene derivative per atom of rhodium.

30. The improvement of claim 29 wherein said olefin is an alkene.

31. The improvement of claim 26 wherein there are maintained in said reaction zone from about 1.5 to about 3.0 moles of said ferrocene derivative per atom of rhodium.

32. The improvement of claim 26 wherein there are maintained in said reaction zone about 1.5 moles of said ferrocene derivative per atom of rhodium.

33. The improvement of claim 26 wherein the structure of the rhodium hyrido carbonyl in complex combination with the ferrocene derivative is

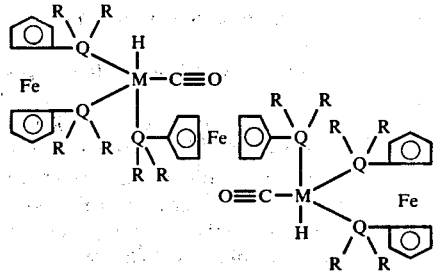

wherein M is rhodium and Q is phosphorous.

34. The improvement of claim 33 wherein R is phenyl.

35. The improvement of claim 26 wherein there are charged to the reaction zone:
a ferrocene derivative of the formula

Fe

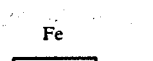

a complex of the formula

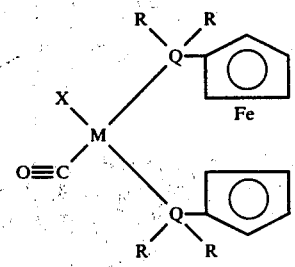

wherein M is rhodium and X is a halide,
and a halide scavenger in an amount at least equivalent to the halide content of said complex, together with a hydride source.

36. The improvement of claim 35 wherein the hydride source is hydrogen and the halide is chloride.

37. The improvement of claim 36 wherein Q is phosphorus.

38. The improvement of claim 37 wherein R is phenyl.

39. The improvement of claim 35 wherein there is maintained in the reaction zone at least about one-half mole of said ferrocene derivative per mole of said complex.

40. The improvement of claim 39 wherein there is maintained in the reaction zone about one-half mole of said ferrocene derivative per mole of said complex.

41. The improvement of claim 26 wherein there are charged to the reaction zone:

a ferrocene derivative of the formula

Fe
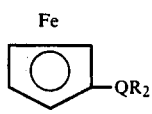

and a complex of the formula

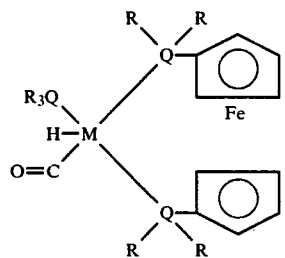

wherein M is rhodium.

42. The improvement of claim 41 wherein Q is phosphorus.

43. The improvement of claim 42 wherein R is phenyl.

44. The improvement of claim 41 wherein there is maintained in the reaction zone at least about one-half mole of said ferrocene derivative per mole of said complex.

45. The improvement of claim 44 wherein there is maintained in the reaction zone about one-half mole of said ferrocene derivative per mole of said complex.

46. The improvement of claim 26 wherein there are charged to the reaction zone a ferrocene derivative of the formula

Fe
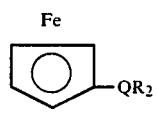

wherein Q is phosphorus and R is phenyl or lower alkyl and a rhodium hydrido carbonyl complex of the formula $$Rh(H)(CO)(X)_3$$

wherein X is trialkylphosphine, triarylphosphine, tricycloalkylphosphine, trialkylphosphite, triarylphosphite, or tricycloalkylphosphite.

47. The improvement of claim 46 wherein R is phenyl.

48. The improvement of claim 47 wherein X is triphenylphosphine.

49. The improvement of claim 46 wherein there are maintained in the reaction zone at least about 1.5 moles of said ferrocene derivative per atom of rhodium.

50. The improvement of claim 49 wherein there are maintained in the reaction zone about 1.5 moles of said ferrocene derivative per atom of rhodium.

* * * * *

UNITED STATES PATENT AND TRADEMARK OFFICE
CERTIFICATE OF CORRECTION

PATENT NO. : 4,193,943
DATED : March 18, 1980
INVENTOR(S) : Jerry Dean Unruh et al.

It is certified that error appears in the above-identified patent and that said Letters Patent are hereby corrected as shown below:

In the Abstract, first line of the second paragraph, after "complex" insert -- it --.

In column 1, line 22, in the structural formula change the moiety "-$OR_3$" to -- -$QR_3$ --.

In column 9, line 4, for "reactiong" read -- reaction --.

In column 10, line 53, for "reactans" read -- reactants --.

In column 12, line 58, for "maintaned" read -- maintained --.

In column 13, last item in first column of Table I, for "Hexene" read -- Hexane --.

In column 13, last item in first column of Table II, for "Hexene" read -- Hexane --.

UNITED STATES PATENT AND TRADEMARK OFFICE
CERTIFICATE OF CORRECTION

PATENT NO. : 4,193,943
DATED : March 18, 1980
INVENTOR(S) : Jerry Dean Unruh et al.

It is certified that error appears in the above-identified patent and that said Letters Patent are hereby corrected as shown below:

In column 14, last item in first column of Table III, for "Hexene" read -- Hexane --.

In column 15, last item in first column of Table IV, for "Hexene" read -- Hexane --.

In column 15, line 60, for "1-hexane" read -- 1-hexene --.

In column 16, line 5, for "disbustituted" read -- disubstituted --.

Signed and Sealed this

Twenty-ninth Day of July 1980

[SEAL]

Attest:

SIDNEY A. DIAMOND

Attesting Officer

Commissioner of Patents and Trademarks